United States Patent
Sommer et al.

(10) Patent No.: US 11,085,985 B2
(45) Date of Patent: Aug. 10, 2021

(54) MAGNETIC RESONANCE FINGERPRINTING IN FOURIER SPACE

(71) Applicant: KONINKLIJKE PHILIPS N.V., Eindhoven (NL)

(72) Inventors: Karsten Sommer, Hamburg (DE); Thomas Erik Amthor, Hamburg (DE); Jan Jakob Meineke, Hamburg (DE); Peter Koken, Hamburg (DE); Mariya Ivanova Doneva, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/627,827

(22) PCT Filed: Jul. 3, 2018

(86) PCT No.: PCT/EP2018/068006
§ 371 (c)(1),
(2) Date: Dec. 31, 2019

(87) PCT Pub. No.: WO2019/007993
PCT Pub. Date: Jan. 10, 2019

(65) Prior Publication Data
US 2020/0166596 A1 May 28, 2020

(30) Foreign Application Priority Data
Jul. 4, 2017 (EP) .................................... 17179547

(51) Int. Cl.
*G01R 33/56* (2006.01)
*A61B 5/00* (2006.01)
(Continued)

(52) U.S. Cl.
CPC ........ *G01R 33/5608* (2013.01); *A61B 5/0042* (2013.01); *A61B 5/055* (2013.01);
(Continued)

(58) Field of Classification Search
CPC ............ G01R 33/5608; G01R 33/4828; G01R 33/543; G01R 33/561; A61B 5/0042; A61B 5/055; A61B 5/7257
See application file for complete search history.

(56) References Cited

U.S. PATENT DOCUMENTS 7,254,500 B2 * 8/2007 Makeig .................. A61B 5/048
324/76.19
9,633,455 B1 * 4/2017 Mailhe ................... G01R 33/50
(Continued)

OTHER PUBLICATIONS

Ma et al "Magnetic Resonance Fingerprinting" Nature vol. 495, p. 187-193 Mar. 13, 2013.
Jang et al "Iterative Compressed Sensing Reconstruction Using Forward Model Based on MIR Multi-Parameter" Proceedings of the International Society for Magnetic Resonance in Med. May 10-16, 2014 vol. 22, p. 4283.
(Continued)

*Primary Examiner* — Dixomara Vargas (57) ABSTRACT

A magnetic resonance imaging (MRI) system includes a memory for storing machine executable instructions and MRF pulse sequence commands. The MRF pulse sequence commands are configured for controlling the MRI system to acquire MRF magnetic resonance data according to a magnetic resonance fingerprinting protocol. The memory further includes a Fourier transformed magnetic resonance finger printing dictionary. The finger printing dictionary includes entries for at least one intrinsic property.

15 Claims, 7 Drawing Sheets

(51) Int. Cl.
*A61B 5/055* (2006.01)
*G01R 33/48* (2006.01)
*G01R 33/54* (2006.01)
*G01R 33/561* (2006.01)

(52) U.S. Cl.
CPC ........ *A61B 5/7257* (2013.01); *G01R 33/4828* (2013.01); *G01R 33/543* (2013.01); *G01R 33/561* (2013.01)

(56) References Cited

U.S. PATENT DOCUMENTS

| | | | | |
|---|---|---|---|---|
| 9,964,616 | B2* | 5/2018 | Cauley | G01R 33/4828 |
| 10,132,900 | B2* | 11/2018 | Grodzki | G01R 33/5608 |
| 10,194,829 | B2* | 2/2019 | Kaditz | A61B 5/055 |
| 10,209,334 | B2* | 2/2019 | Cohen | G01R 33/54 |
| 10,222,441 | B2* | 3/2019 | Kaditz | G01R 33/48 |
| 10,359,486 | B2* | 7/2019 | Kaditz | G01N 24/08 |
| 10,379,189 | B2* | 8/2019 | Gulani | A61B 5/0035 |
| 10,386,433 | B2* | 8/2019 | Fenchel | G01R 33/4828 |
| 10,492,710 | B2* | 12/2019 | Wang | A61B 5/055 |
| 2005/0007091 | A1* | 1/2005 | Makeig | G06K 9/624 324/76.13 |
| 2014/0103924 | A1 | 4/2014 | Griswold | |
| 2014/0180146 | A1* | 6/2014 | Nicoli | A61B 6/507 600/504 |
| 2014/0303478 | A1 | 10/2014 | Roche et al. | |
| 2015/0346301 | A1* | 12/2015 | Cauley | G01R 33/4828 324/309 |
| 2016/0025835 | A1* | 1/2016 | Gulani | A61B 5/0035 600/420 |
| 2016/0061922 | A1* | 3/2016 | Grodzki | G01R 33/5608 324/309 |
| 2016/0097830 | A1* | 4/2016 | Grodzki | A61B 5/055 324/309 |
| 2016/0259022 | A1* | 9/2016 | Beck | G01R 33/50 |
| 2016/0282430 | A1 | 9/2016 | Gulani et al. | |
| 2016/0282434 | A1 | 9/2016 | Seiberlich et al. | |
| 2016/0299206 | A1* | 10/2016 | Cohen | G01R 33/54 |
| 2017/0319098 | A1* | 11/2017 | Wang | A61B 5/055 |

OTHER PUBLICATIONS

Alon et al "Subject Specific Body Model Creation Using MR Fingerprinting" Proc. of the Int. Proc. for Magnetic Reson. in Med. vol. 23, May 15, 2015 p. 299.

Zaheer Abbas et al., "Analysis of Proton-Density Bias Corrections Based on T1 Measurement for Robust Quantification of Water Content in the Brain at 3 Tesla" Magnetic Resonance in Med. 72 p. 1735-1745 (2014).

R. Venkatesan et al., Absolute Measurements of Water Content Using Magnetic Resonance Imaging: Preliminary Findings in an In Vivo Focal Ischemic Rat Model; Magnetic Resonance in Med. 43 p. 146-150 (2000).

P. P. Fatouros et al., In Vivo Brain Water Determination by TI Measurements: Effect of Total Water Content, Hydration Fraction, and Field Strength; Magnetic Resonance in Med. 17 p. 402-413 (1991).

R. L. Kamman et al., Nuclear Magnetic Resonance Relaxation in Experimental Brain Edema: Effects of Water Concentration, Protein Concentration, and Temperature; Magnetic Resonance in Med. 6 p. 265-274 (1988).

International Search Report and Written Opinion from PCT/EP2018/068006 dated Oct. 24, 2018.

Neeb et al "A New Method for Fast Quantitative Mapping of Absolute Water Content In Vivo" Neuroimage 31 (2006) p. 1156-1168.

Neeb "Fast Quantitiative Mapping of Absolute Water Content With Full Brain Coverage" Neuroimage 42 (2008) p. 1094-1109.

Oros-Peusquens et al "A 7 Min. Prototcol for Quantitative,Whole-Brain, Accurate Water Mapping at 3T for Neurological Applications" Proc. Intl. Soc. Mag. Reson Med. 20 (2012) p. 4270.

Jiang et al "Mr Fingerprinting Using Fast Imaging With Steady State Precession With Spiral Readout" Magn. Reson. in Med. 74 p. 1621-1631 (2015).

Deshmane et al "Enforcing a Physical Tissue Model for Partial Volume MR Fingerprinting" Proc. Intl. Soc. Mag. Reson. Med. 24 (2016) p. 2995-2998.

Volz et al "Correction of Systematic Errors in Quatitative Proton Density Mapping" Magn. Reson. in Med. 68 p. 74-85 (2012).

* cited by examiner

MAGNETIC RESONANCE FINGERPRINTING IN FOURIER SPACE

CROSS REFERENCE TO RELATED APPLICATIONS

This application is a U.S. national phase application of International Application No. PCT/EP2018/068006 filed Jul. 3, 2018, which claims the benefit of EP Application Serial No. 17179547,9 filed on Jul. 4, 2017 and is incorporated herein by reference.

FIELD OF THE INVENTION

The invention relates to Magnetic Resonance Imaging, in particular to Magnetic Resonance Fingerprinting techniques.

BACKGROUND OF THE INVENTION

Magnetic Resonance fingerprinting (MRF) is a technique where a number of RF pulses, distributed in time, are applied such that they cause signals from different materials or tissues to have a unique contribution to the measured Magnetic Resonance (MR) signal. A limited dictionary of precalculated signal contributions from a set or fixed number of substances is compared to the measured MR signals. This can for example be used to determine intrinsic properties such as T1, T2, and B1+ values. In other examples, the comparison between a dictionary of precalculated signals and the measured signal can be used to determine the material composition within a single voxel. For example if it is known that a voxel only contains water, fat, and muscle tissue the contribution from these three materials need only be considered and intra-voxel component matching can be used to accurately determine the composition of the voxel. The magnetic resonance fingerprinting technique was introduced in the journal article Ma et al., "Magnetic Resonance Fingerprinting," Nature, Vol. 495, pp. 187 to 193, doi: 10.1038/nature 11971.

SUMMARY OF THE INVENTION

The invention provides for a magnetic resonance imaging system, a computer program product, and a method in the independent claims. Embodiments are given in the dependent claims.

The Nature article by Ma et al. introduces the basic idea of magnetic resonance fingerprinting and terminology which is used to describe this technique such as the dictionary. In the present invention, magnetic resonance fingerprinting is performed using a Magnetic Resonance Fingerprinting signal that has been Fourier transformed and matches it to a magnetic resonance fingerprinting dictionary that has also been Fourier transformed. This may have the advantage of enabling magnetic resonance fingerprinting to be performed using a higher degree of undersampling and thereby enable acceleration of the MRF protocol. As the degree of undersampling is increased, there will be an increasing number of artifacts in the MRF signal which appear as noise or high temporal frequency oscillations in the signal. Embodiments may provide for an improved means of rejecting the undersampling artifacts by matching a temporal Fourier transformed MRF signal to Fourier transformed MRF dictionary. During this matching process, the number of terms of the Fourier transformed MRF signal in the temporal frequency domain is limited to a predetermined number of terms. The high frequency sampling artifacts are effectively filtered out and only the low frequency behavior of the MRF signal is used for the matching.

In one aspect, the invention provides for a magnetic resonance imaging system comprising a memory for storing machine-executable instructions and for storing MRF pulse sequence commands. MRF is an acronym for magnetic resonance fingerprinting. MRF pulse sequence commands is a label for particular pulse sequence commands. Pulse sequence commands as used herein encompass either instructions which can be used directly for controlling the magnetic resonance imaging system according to a magnetic resonance imaging protocol or data which can be converted by a processor into such instructions. For example typically pulse sequence commands are laid out as a series of timing diagrams. This information or data used for representing or storing the timing diagram may be used to generate pulse sequence commands. The MRF pulse sequence commands are configured for controlling the magnetic resonance imaging system to acquire MRF magnetic resonance data according to a magnetic resonance fingerprinting protocol. The memory further contains a Fourier transform magnetic resonance fingerprinting dictionary. A Fourier transform magnetic resonance fingerprinting dictionary is a magnetic resonance fingerprinting dictionary that has been temporarily Fourier transformed into a frequency spectral distribution; the Fourier transformation is along the time-progress of the MRF signal evolution The Fourier transform magnetic resonance fingerprinting dictionary comprises entries for at least one intrinsic property. An intrinsic property as used herein encompasses any property which may be determined using magnetic resonance imaging that varies as a position of location. Examples include the concentrations or relative concentrations of various types of tissue or material. Other examples may be the value of a magnetic field such as the T1 value, T2 value, B0, or B1+, or B1− fields.

The magnetic resonance imaging system further comprises a processor for controlling the magnetic resonance imaging system. Execution of the machine-executable instructions causes the processor to acquire the MRF magnetic resonance data descriptive of a region of interest by controlling the magnetic resonance imaging system with the MRF pulse sequence commands. The region of interest is divided into voxels. Execution of the machine-executable instructions further causes the processor to construct an MRF signal, i.e. a signal evolution along the (e.g pseudo-random) variations of image parameters (such as flip angle) as time progresses, for each of the voxels using the MRF magnetic resonance data. When magnetic resonance fingerprinting is performed there is a train of pulse sequence commands where various parameters in each of the pulse repetitions is varied. For each of these pulse repetitions an image is acquired. The MRF signal is the value of the voxel for each of these series of images taken as a sequence. Execution of the machine-executable instructions further causes the processor to construct a Fourier transformed MRF signal by Fourier transforming the MRF signal for each of the voxels. Each of the voxels has an MRF signal that is constructed. Then this signal is Fourier transformed. Execution of the machine-executable instructions further causes the processor to determine the at least one intrinsic property for each of the voxels using the Fourier transformed MRF signal and the Fourier transform magnetic resonance fingerprinting dictionary. The Fourier transformed MRF signal is truncated to a predetermined number of terms before determining the at least one intrinsic property.

In this embodiment, both the MRF signal and the magnetic resonance fingerprinting dictionary are both Fourier transformed and the matching is performed with the Fourier transformed MRF signal and the Fourier transformed dictionary. This may have the advantage that it enables accurate magnetic resonance fingerprinting to be performed even when the data is highly undersampled or if there is initial noise. Truncating the temporal Fourier transformed MRF signal in the temporal frequency domain to a predetermined number of terms may also be beneficial in that it reduces the effect of high-frequency noise or artifacts due to undersampling. This procedure may enable MRF fingerprinting that provides for improved accuracy and/or consistency.

In another embodiment, execution of the machine-executable instructions further cause the processor to calculate a magnetic resonance fingerprinting dictionary by modeling each of the predetermined substances as a single spin with the Bloch equations for each of the discrete voxels. After calculating the magnetic resonance fingerprinting dictionary, the Fourier transformed magnetic resonance finger printing dictionary is calculated by Fourier transforming the entries in the magnetic resonance fingerprinting dictionary. For example, in each of the discrete voxels a hypothetical spin can be modeled using the Bloch equations and a simulation of the magnetic resonance system using the MRF pulse sequence instructions. The calculated magnetic resonance data at each of the sampling times is then the magnetic resonance fingerprinting dictionary for the particular type of spin that was modeled. This would function particularly well for the case where the measurement zone is only divided into a single voxel. It also applies to the case where there is no gradient magnetic field for spatial encoding. For example, the magnetic resonance system could be a so-called NMR system for doing a chemical analysis on a sample. The entries of the Fourier transformed magnetic resonance finger printing dictionary can, in some examples, be truncated to the predetermined number of terms.

In another embodiment, the method further comprises calculating the magnetic resonance fingerprinting dictionary by modeling each of the predetermined substances as between 5 and 1 spins with the Bloch equation for each of the discrete voxels. After calculating the magnetic resonance fingerprinting dictionary, the Fourier transformed magnetic resonance finger printing dictionary is calculated by Fourier transforming the entries in the magnetic resonance fingerprinting dictionary. The entries of the Fourier transformed magnetic resonance finger printing dictionary can, in some examples, be truncated to the predetermined number of terms.

In another embodiment, the method further comprises calculating the magnetic resonance fingerprinting dictionary by modeling each of the predetermined substances with the Bloch equation for each of the discrete voxels. After calculating the magnetic resonance fingerprinting dictionary, the Fourier transformed magnetic resonance finger printing dictionary is calculated by Fourier transforming the entries in the magnetic resonance fingerprinting dictionary. The entries of the Fourier transformed magnetic resonance finger printing dictionary can, in some examples, be truncated to the predetermined number of terms.

In another embodiment, the at least one intrinsic property comprises combined T1 and T2 values. That is to say the magnetic resonance fingerprinting dictionary is constructed and has entries for a matrix of T1 and T2 values. The determining of the at least one intrinsic property comprises determining a combined T1 and T2 value for each of the voxels using the Fourier transformed MRF signal and the matrix of combined T1 and T2 values in the Fourier transformed magnetic resonance fingerprinting dictionary. This embodiment may be beneficial because taking just the T1 and T2 values an accurate representation of the MRF signal can be constructed.

In another embodiment, the Fourier transformed magnetic resonance fingerprinting dictionary comprises a model Fourier transformed MRF signal for each of the matrix of the T1 and T2 values. The method further comprises constructing a proton density map by calculating a scaling factor for each voxel between the model Fourier transformed MRF signal of the combined T1 and T2 value and the Fourier transformed MRF signal. This embodiment may be beneficial because it provides an efficient means of constructing a proton density map when the MRF magnetic resonance data is undersampled or highly undersampled.

In another embodiment, the Fourier transformed magnetic resonance fingerprinting dictionary further comprises entries for a set of predetermined substances. The predetermined substances for example may be different materials or tissue types. The local quantity of a particular predetermined substance therefore qualifies as an intrinsic property. Execution of the machine-executable instructions further causes the processor to calculate an intra-voxel component mapping for each of the voxels using the entries for the set of predetermined substances and the Fourier transformed MRF signal. Execution of the machine-executable instructions further causes the processor to calculate a total water content map by scaling the proton density map using the intra-voxel component mapping. This embodiment may be beneficial because it provides for an accurate means of determining the total water content map.

An entry in a magnetic resonance fingerprinting dictionary encompasses a measured or computationally modeled MRF signal for a particular intrinsic property.

In another embodiment, the predetermined substances comprise fat. Calculating the intra-voxel component mapping comprises determining a fat mapping. Execution of the machine-executable instructions further cause the processor to correct the total water content map using the fat mapping. This embodiment may be beneficial because it prevents fat or adipose tissue from being falsely interpreted as being water tissue or tissue that contains much water. This may be very useful in correcting the total water content map.

In another embodiment, the predetermined substances comprise cerebrospinal fluid. Execution of the machine-executable instructions further causes the processor to identify CSF voxels at least partially by identifying voxels with a fraction of the cerebrospinal fluid in the intra-voxel component mapping above a predetermined threshold. The scaling of the proton density map into the total water content map is performed using a scaling factor determined using the CSF voxels. In this embodiment if a voxel is identified as containing all or CSF fluid above a certain threshold then the composition of the material inside the voxel can be accurately determined. The water content of these voxels that are all or mostly filled with CSF fluid can then be used to scale and correct the total water content map.

In another embodiment, the predetermined substances comprise cerebrospinal fluid. The intra-voxel component mapping for these voxels is calculated by maximizing an inner product of the Fourier transformed MRF signal with entries for the set of predetermined substances. Execution of the machine-executable instructions further causes the processor to identify CSF voxels at least partially by identifying voxels which have an inner product between the Fourier transformed MRF signal and the entry for the cerebrospinal fluid in the Fourier transformed magnetic resonance fingerprinting dictionary above a predetermined threshold. The scaling of the proton density map into the total water content map is performed using a scaling factor determined using the CSF voxels.

This embodiment may be beneficial because when the dictionaries matching is performed using the inner product method, the component, which is indicated as being the most likely constituent of that voxel, may have a poor match nonetheless. For example, a flow of the cerebrospinal fluid may corrupt the magnetic resonance fingerprinting signal. This signal may be sufficient to correctly identify the content of a voxel as being all or mostly CSF fluid but the value, which would be useful for scaling the total water content map, may not be sufficient accurate. By limiting the identification of the CSF voxels to voxels which have an inner product above a predetermined threshold, all sorts of additional errors, which would not be otherwise caught, are automatically sorted out and the quality of the total water content map may be vastly improved.

In another embodiment, the magnetic resonance imaging system comprises a sample with a predetermined water concentration. For example, the sample may be a water vial or a container of other material which is placed on the surface or adjacent to the subject. Execution of the machine-executable instructions further causes the processor to identify voxels containing the sample in the intra-voxel component mapping. The scaling of the proton density map into the total water content map is performed using the scaling factor determined using voxels containing the sample.

In another embodiment, the predetermined substances comprise gray matter. The predetermined substances comprise white matter. Execution of the machine-executable instructions cause the processor to calculate a GM or gray matter mask by identifying voxels above a predetermined gray matter concentration in the intra-voxel component mapping. Execution of the machine-executable instructions further cause the processor to calculate a WM or white matter mask by identifying voxels above a predetermined white matter concentration in the intra-voxel component mapping. Execution of the machine-executable instructions further causes the processor to correct the proton density map with a bias field by fitting a function to the proton density map that reduces signal variation in voxels identified by the GM mask and WM mask. The fitting of the function to the proton density map is equivalent to determining the bias field. This embodiment may be beneficial because it may provide for a superior means of correcting for the bias field.

In another embodiment, the predetermined substances comprise cerebrospinal fluid. The predetermined substances comprise gray matter. The predetermined substances comprise white matter. Execution of the machine-executable instructions causes the processor to calculate a GM mask by identifying voxels above a predetermined gray matter concentration in the intra-voxel component mapping. Execution of the machine-executable instructions further causes the processor to calculate a WM mask by identifying voxels above a predetermined white matter concentration in the intra-voxel component mapping. Execution of the machine-executable instructions further cause the processor to calculate a pseudo proton density map using the concentration mapping. The pseudo proton density map is constructed by assembling all of the constituents of the particular voxel according to the intra-voxel component mapping. This can then be used to infer or calculate a proton density map. This is the pseudo proton density map.

Execution of the machine-executable instructions further causes the processor to correct the proton density map with a bias field by fitting a function to the pseudo proton density map that reduces signal variation in voxels identified by the GM mask and the WM mask. In this embodiment the pseudo proton density map makes a mapping of the proton density using the concentration sampling. The concentration mapping can also be used to identify voxels that are essentially filled with gray matter or white matter. The composition of the gray matter and the white matter in a particular individual should be very uniform. For this reason, the voxels identified by the GM mask and the WM mask can be used to calculate a correction that is equivalent to the bias field by making the intensity or signal variation in voxels of the GM mask and the WM mask within certain ranges.

In another embodiment, execution of the machine-executable instructions further cause the processor to identify filled voxels in the intra-voxel component mapping with a concentration above a predetermined threshold for any one of the predetermined substances. Execution of the machine-executable instructions further causes the processor to construct a B1− map at least partially by normalizing the intra-voxel component mapping of the filled voxels. Execution of the machine-executable instructions further causes the processor to correct the proton density map using the B1 mapping. This may provide an alternative means of calculating the bias field.

In another embodiment, the memory further contains B1+ mapping pulse sequence commands for acquiring B1+ mapping magnetic resonance data according to a B1+ mapping magnetic resonance imaging protocol. Execution of the machine-executable instructions further cause the processor to acquire the B1+ mapping magnetic resonance data by controlling the magnetic resonance imaging system with the B1+ mapping pulse sequence commands. Execution of the machine-executable instructions further cause the processor to construct a B1+ mapping using the B1+ mapping magnetic resonance data according to a B1+ mapping magnetic resonance imaging protocol. Execution of the machine-executable instructions further cause the processor to correct the proton density map using the B1+ mapping. In this embodiment an additional pulse sequence is used to explicitly measure the B1+ mapping. This may be beneficial because it may be helpful in correcting the proton density map.

In another embodiment, the at least one intrinsic property comprises B1+ values. In this embodiment the B1+ values are encoded into the magnetic resonance fingerprinting dictionary. The execution of the machine-executable instructions cause the processor to reconstruct a B1+ map using the MRF magnetic resonance data and the Fourier transformed magnetic resonance fingerprinting dictionary. Execution of the machine-executable instructions further cause the processor to correct the proton density map using the B1+ mapping.

In another embodiment, the MRF pulse sequence commands are configured for acquiring MRF magnetic resonance data using flip angles that vary sequentially according to a sinusoidal distribution.

In another embodiment, the MRF pulse sequence commands are configured for acquiring MRF magnetic resonance data with a spiral trajectory in k-space. This embodiment may be beneficial because using a spiral trajectory with high undersampling and different undersampling for different TRs results in incoherent (noise-like) undersampling artifacts in the image series and along the temporal direction. These incoherent artifacts can be filtered out by truncating the Fourier transformed MRF signal to a predetermined number of initial terms.

In another embodiment, the MRF pulse sequence commands are configured for undersampling the MRF magnetic resonance data.

In another embodiment, the MRF pulse sequence commands are configured for undersampling the MRF magnetic resonance data with a high undersampling factor.

In another embodiment, the Fourier transformed magnetic resonance fingerprinting dictionary further comprises entries for a set of predetermined substances. The determining of the at least one intrinsic property comprises calculating an intra-voxel component mapping for each of the voxels using the entries for the set of predetermined substances and the Fourier transformed MRF signal. This embodiment may be beneficial because it may provide for an efficient means of calculating the intra-voxel component mapping even when there is very high undersampling during the MRF protocol.

In another aspect, the invention provides for a method of operating the magnetic resonance imaging system. The method comprises acquiring MRF magnetic resonance data descriptive of a region of interest by controlling the magnetic resonance imaging system with the MRF pulse sequence commands. The MRF pulse sequence commands are configured for controlling the magnetic resonance imaging system to acquire MRF magnetic resonance data according to a magnetic resonance fingerprinting protocol. The region of interest is divided into voxels. The method further comprises constructing an MRF signal for each of the voxels using the MRF magnetic resonance data. The method further comprises constructing a Fourier transformed MRF signal by Fourier transforming the MRF signal for each of the voxels. The method further comprises determining at least one intrinsic property for each of the voxels using the Fourier transformed MRF signal and a Fourier transformed magnetic resonance fingerprinting dictionary. The Fourier transformed magnetic resonance fingerprinting dictionary comprises entries for the at least one intrinsic property. The Fourier transformed MRF signal is truncated through a predetermined number of terms before determining the at least one intrinsic property. The advantages of this embodiment have been previously discussed.

In another aspect, the invention provides for a computer program product comprising machine-executable instructions for execution by a processor controlling the magnetic resonance imaging system. Execution of the instructions causes the processor to acquire MRF magnetic resonance data descriptive of a region of interest by controlling the magnetic resonance imaging system with the MRF pulse sequence commands. The MRF pulse sequence commands are configured for controlling the magnetic resonance imaging system to acquire MRF magnetic resonance data according to a magnetic resonance fingerprinting protocol. The region of interest is divided into voxels. Execution of the instructions further causes the processor to construct an MRF signal for each of the voxels using the MRF magnetic resonance data. Execution of the machine-executable instructions further cause the processor to construct a Fourier transformed MRF signal by Fourier transforming the MRF signal for each of the voxels. Execution of the machine-executable instructions further cause the processor to determine at least one intrinsic property for each of the voxels using the Fourier transformed MRF signal and a Fourier transformed magnetic resonance fingerprinting dictionary. The Fourier transformed magnetic resonance fingerprinting dictionary comprises entries for the at least one intrinsic property. The Fourier transformed MRF signal is truncated to a predetermined number of terms before determining the at least one intrinsic property. The advantages of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two or three dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
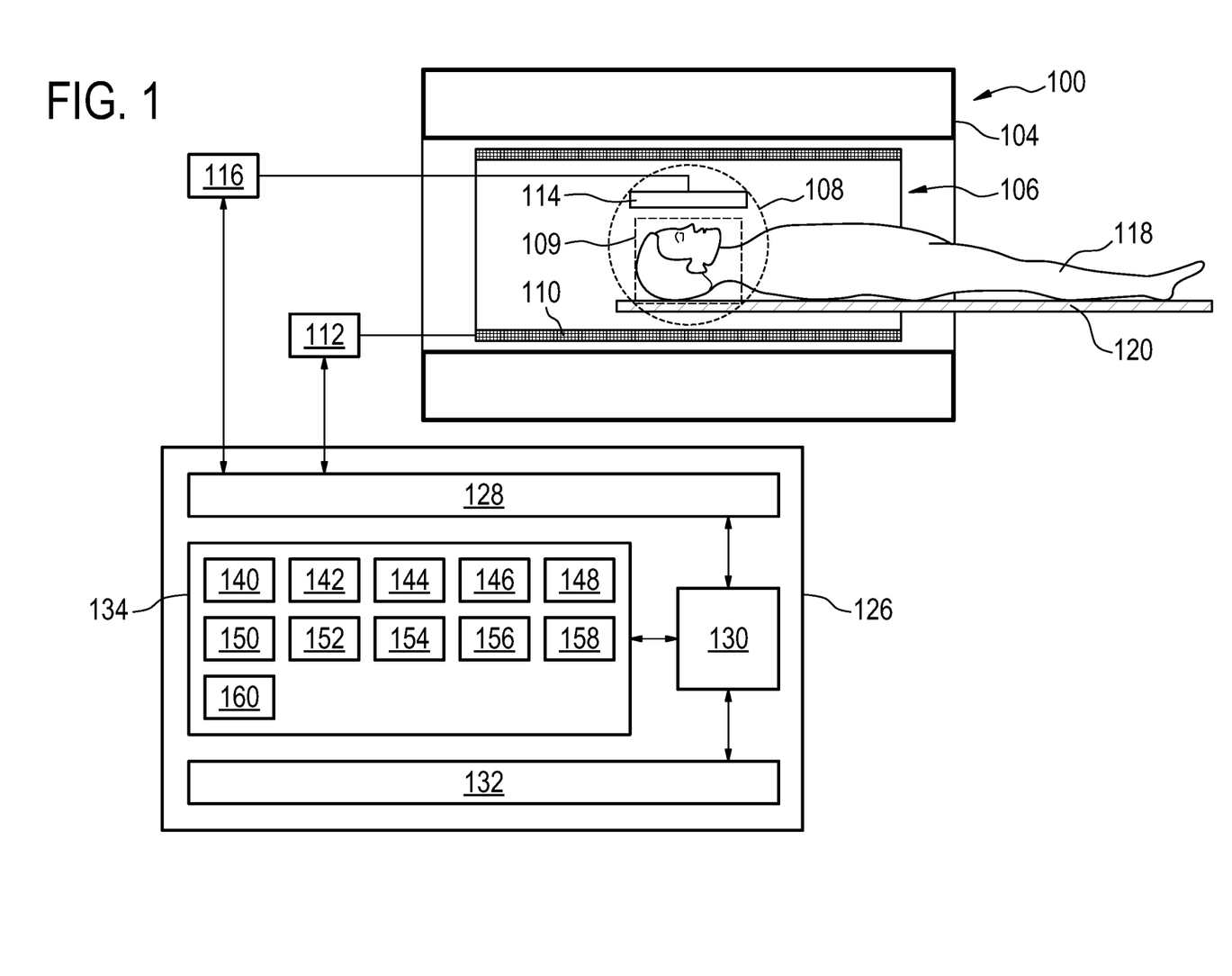
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. A subject 118 is shown as being supported by a subject support 120 such that at least a portion of the subject 118 is within the imaging zone 108 and the region of interest 109.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels. For example if a parallel imaging technique such as SENSE is performed, the radio-frequency could 114 will have multiple coil elements.

In this example the subject, 118 is positioned such that the subject's head region is within the region of interest 109. In other examples, other parts of the subject's 118 body may be positioned in the region of interest 109.

The transceiver 116 and the gradient controller 112 are shown as being connected to a hardware interface 128 of a computer system 126. The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 130 may be considered to be a non-transitory computer-readable medium.

The computer memory 134 is shown as containing machine-executable instructions 140 which enable the processor 130 to control the magnetic resonance imaging system 100. The computer memory 134 is further shown as containing MRF pulse sequence commands 142. The MRF pulse sequence commands 142 contain instructions 130 which enable the processor to control the magnetic resonance imaging system 100 such that it can acquire MRF magnetic resonance data 144. Once the processor 130 has used the magnetic resonance imaging system 100 to acquire the MRF magnetic resonance data 144 the processor 130 may calculate an MRF signal 146 from the magnetic resonance data 144. The magnetic resonance data 144 is a series of data which may be constructed into individual images. The data for a particular voxel is arranged in a series to construct the MRF signal 146.

The computer memory 134 is further shown as containing a Fourier transformed MRF signal. The Fourier transformed MRF signal 148 is a Fourier transform of the MRF signal 146. The Fourier transformed MRF signal 148 may also then at this point be truncated to a predetermined number of initial terms. The computer memory 134 is further shown as containing a Fourier transformed magnetic resonance fingerprinting dictionary 150. The Fourier transformed magnetic resonance fingerprinting dictionary 150 may be a magnetic resonance fingerprinting dictionary that has been Fourier transformed. This enables direct matching of the Fourier transformed MRF signal 148 with the Fourier transformed entries in the Fourier transformed magnetic resonance fingerprinting dictionary 150.

The computer memory 134 is further shown as containing an intrinsic property mapping 152 that was obtained by matching the Fourier transformed MRF signal 148 to the Fourier transformed magnetic resonance fingerprinting dictionary 150. The computer memory 134 is shown as optionally containing a combined T1 and T2 mapping 154. Entries may be constructed for the Fourier transformed magnetic resonance fingerprinting dictionary to form a matrix for a combined T1 and T2 value. The combined T1 and T2 mapping 154 is an example of one type of intrinsic property 152 that can be mapped. The computer memory 134 is also shown as optionally containing a proton density map 156 that was constructed by scaling the T1 and T2 mapping 154 to the entry in the Fourier transformed magnetic resonance fingerprinting dictionary. For example the Fourier transformed magnetic resonance fingerprinting dictionary comprises a model for a transformed MRF signal for each of a matrix of T1 and T2 values.

The proton density is then calculated by determining a scaling factor for each voxel between the model Fourier transform signal of the combined T1 and T2 value and the Fourier transformed MRF signal. The computer memory 134 is also shown as optionally containing a total water content map 158 that was calculated using the proton density map 156 and a further scaling factor according to an example. The total water content map 158 could be scaled using several different means. In FIG. 1 the head region of the subject 118 is examined. Using an intrinsic property mapping 152 the regions of cerebrospinal fluid could be identified and used to provide a scaling factor to scale the proton density map 156 into the total water content map 158. This is merely an example and one of several ways of doing this. The computer memory 134 is further shown as optionally containing an intra-voxel content mapping 160. The intra-voxel content mapping 160 is a mapping which identifies the material contents of each of the voxels. For example it may identify such things as water, fat, or even tissue type or pathological tissue type. This may be performed by having entries for a set of predetermined substances in the Fourier transformed magnetic resonance fingerprinting dictionary. The intra-voxel content mapping 160 is a further example of an intrinsic property mapping 152.

Figure 2:
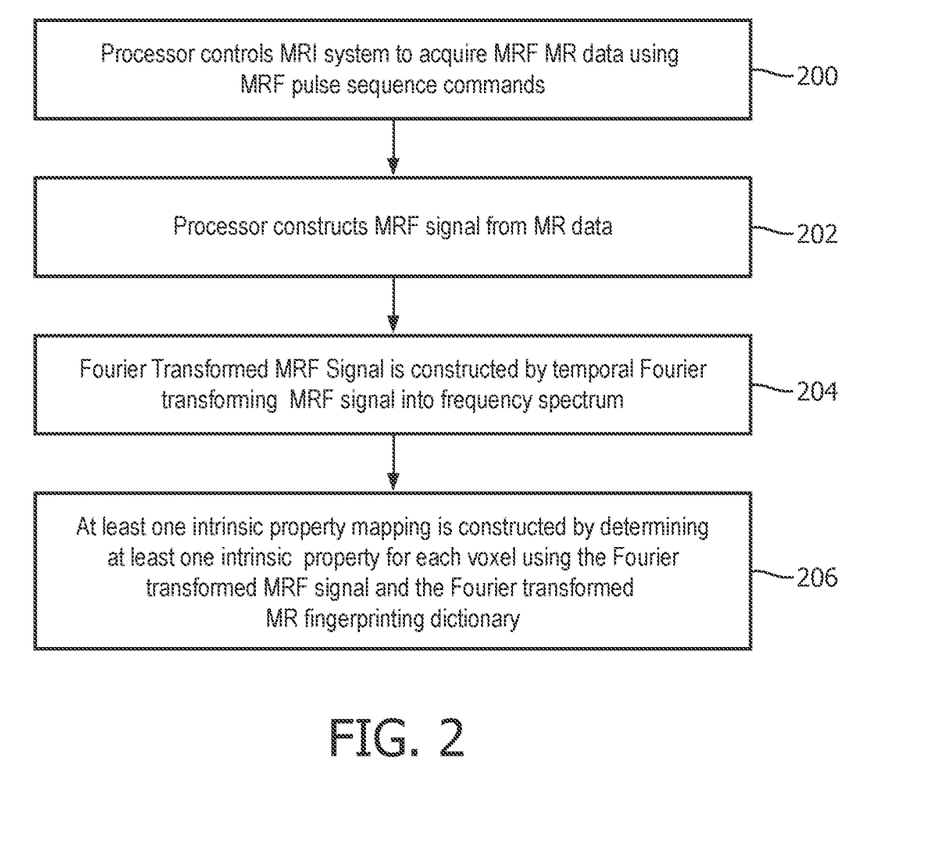
FIG. 2 illustrates an example of a method of operating the magnetic resonance imaging system of FIG. 1.

FIG. 2 shows a flowchart which illustrates a method of operating the magnetic resonance imaging system 100 of FIG. 1. First, in step 100, the processor 130 controls the magnetic resonance imaging system 100 to acquire the MRF magnetic resonance data 144 using the MRF pulse sequence commands 142. This is performed for the region of interest 109. The region of interest 109 is divided into voxels.

Next, in step 202, the processor 130 constructs the MRF signal 146 from the magnetic resonance data 144. Next, in step 204, a Fourier transformed MRF signal 148 is constructed by temporal Fourier transforming the MRF signal 146 into its frequency spectrum. At this step the Fourier transformed MRF signal 148 may be truncated to a predetermined number of initial Fourier temporal frequency components. Finally, in step 206, at least one intrinsic property mapping 152 is constructed by determining at least one intrinsic property for each of the voxels using the Fourier transformed MRF signal 148 and the Fourier transformed magnetic resonance fingerprinting dictionary 150. This may be performed in a number of different ways but is typically performed by finding an inner product between the Fourier transformed MRF signal 148 and entries of calculated or empirically measured MRF signals in the Fourier transformed magnetic resonance fingerprinting dictionary 150. The matching is then performed by optimizing or maximizing the inner product.

Figure 3:
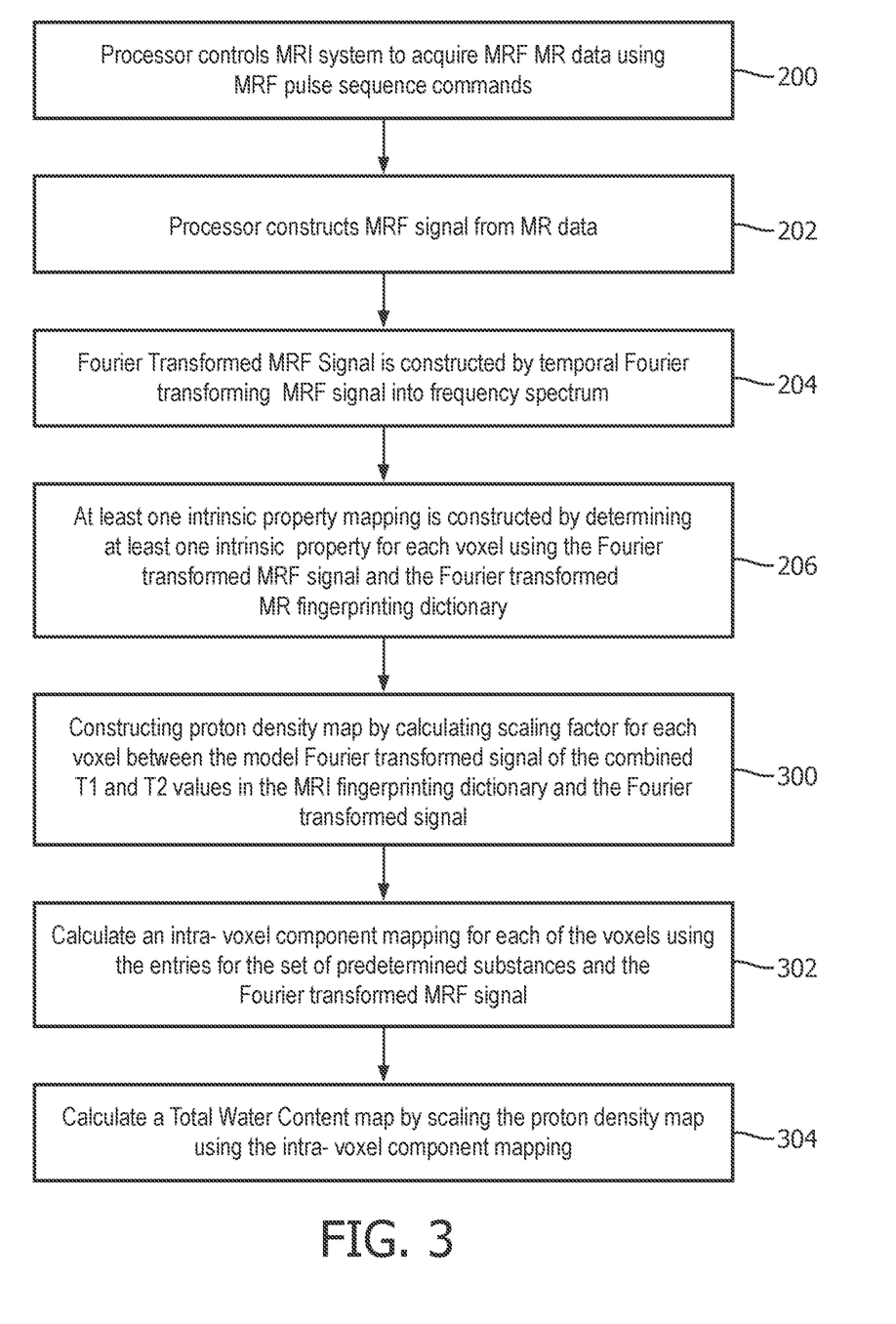
FIG. 3 illustrates a further example of a method of operating the magnetic resonance imaging system of FIG. 1.

FIG. 3 shows a flowchart which illustrates a further example of a method of operating the magnetic resonance imaging system 100 of FIG. 1. The method illustrated in FIG. 3 is similar to the method in FIG. 2. Steps 200-206 are performed again. In this example, in step 206, the intrinsic property mapping 152 is actually the T1 and T2 combined mapping 154. After performing step 206 the method proceeds to step 300. In step 300 the method further comprises constructing a proton density map 156 by calculating the scaling factor for each voxel between the model Fourier transformed signal of the combined T1 and T2 values in the MRF fingerprinting dictionary and the Fourier transformed signal 148. Next, in step 302, execution of the machine-executable instructions further causes the processor 130 to calculate an intra-voxel component mapping 160 for each of the voxels using the entries for the set of predetermined substances in the Fourier transformed MRF dictionary and the Fourier transformed MRF signal 148. Finally, in step 304, the processor 130 calculates a total water content map 158 by scaling the proton density map 156 using the intra-voxel component mapping 160. As mentioned previously, this may be performed in a variety of different ways. As, in this example, the subject's 118 head is within the region of interest 109, cerebrospinal fluid can be located in the intra-voxel content mapping 160 and used to accurately scale the proton density map 156 to the total water content map 158.

Figure 4:
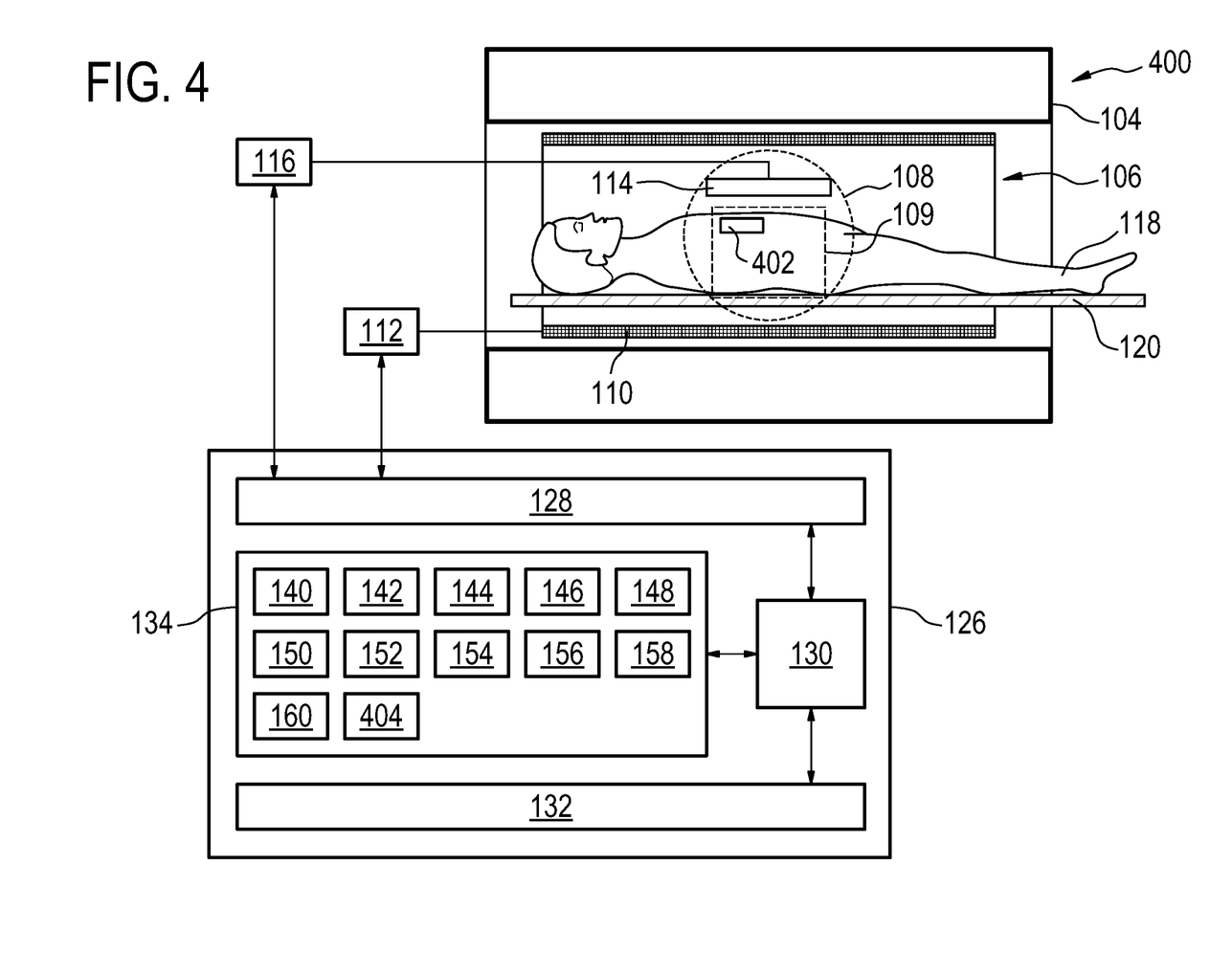
FIG. 4 illustrates a further example of a magnetic resonance imaging system.

FIG. 4 illustrates a further example of the magnetic resonance imaging system 400 that is similar to the magnetic resonance imaging system 100 in FIG. 1. In this example the subject 118 has been positioned such that the region of interest 109 encompasses the subject's 118 abdomen. For constructing a total water content map then the mapping of cerebrospinal fluid in the brain cannot be used. It can be seen that there has been a sample 402 where a known water content has been placed on a surface of the subject 118 within the region of interest 109. The intra-voxel content mapping 160 will then contain a region which is represented by the sample 402. This can be used to create a water content scaling factor 404 using the known water content of the sample 402. The water content scaling factor 404 can then be used to directly scale the proton density map 156 to the total water content map 158.

Figure 5:
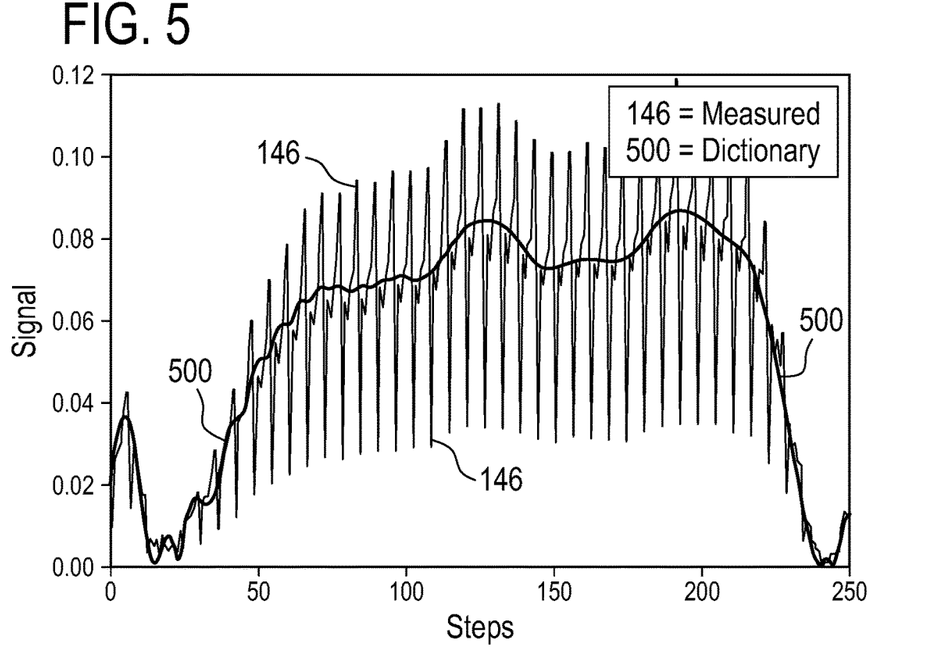
FIG. 5 illustrates an example of a measured MRF signal and a MRF dictionary entry.
Figure 6:
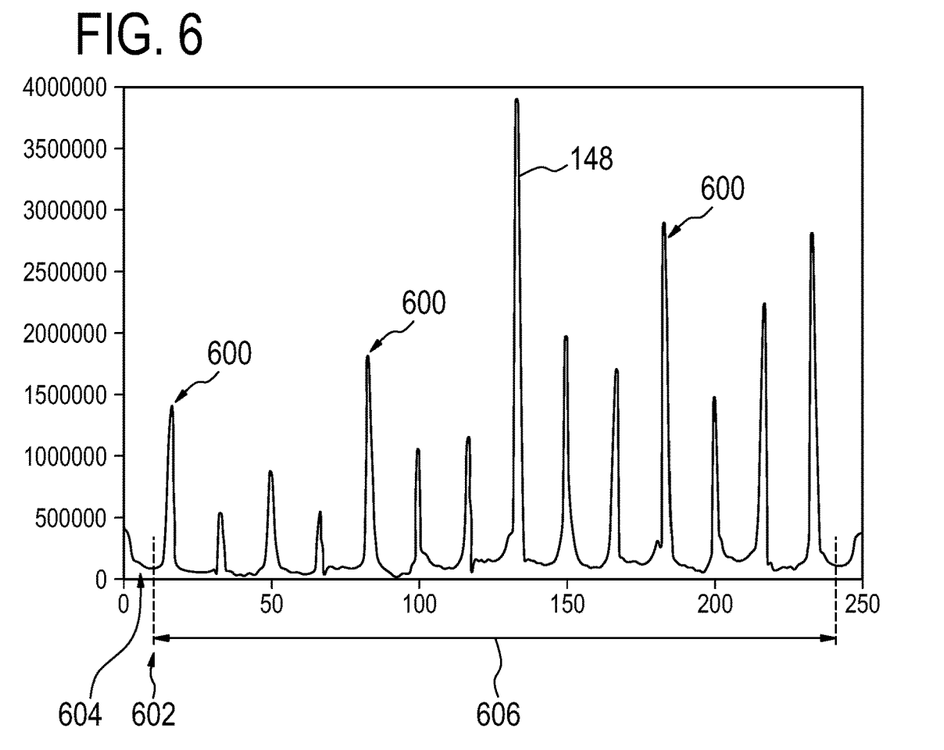
FIG. 6 shows a Fourier transform of the MRF signal of FIG. 5.

FIG. 5 compares an MRF signal 146 and a magnetic resonance fingerprinting dictionary entry 500. In this example the MRF signal 146 is highly undersampled and it can be seen that there are many high-frequency oscillations. The MRF dictionary entry 500 is in contrast extremely smooth. It may be possible to match the MRF signal 146 to the dictionary entry 500; however, the quality may be unreliable or inconsistent due to the aliasing artifacts. FIG. 6 illustrates the Fourier transformed MRF signal 148 for the MRF signal 146. It can be seen that there are a large number of aliasing artifacts 600. The line labeled 602 is a threshold or cut off, which is used to determine the location of the predetermined number of terms 604 for truncating the Fourier transformed MRF signal 148.

The terms indicated by the arrow 606 are excluded from the matching between the Fourier transformed MRF signal 148 and the Fourier transformed magnetic resonance fingerprinting dictionary 150. The terms in the area labeled 604 are consistent and do an excellent job of representing the magnetic resonance fingerprint. The aliasing artifacts 600 are excluded and thus do not have a significant effect on the matching between the Fourier transformed MRF signal 148 and the Fourier transformed magnetic resonance fingerprinting dictionary.

Figure 7:
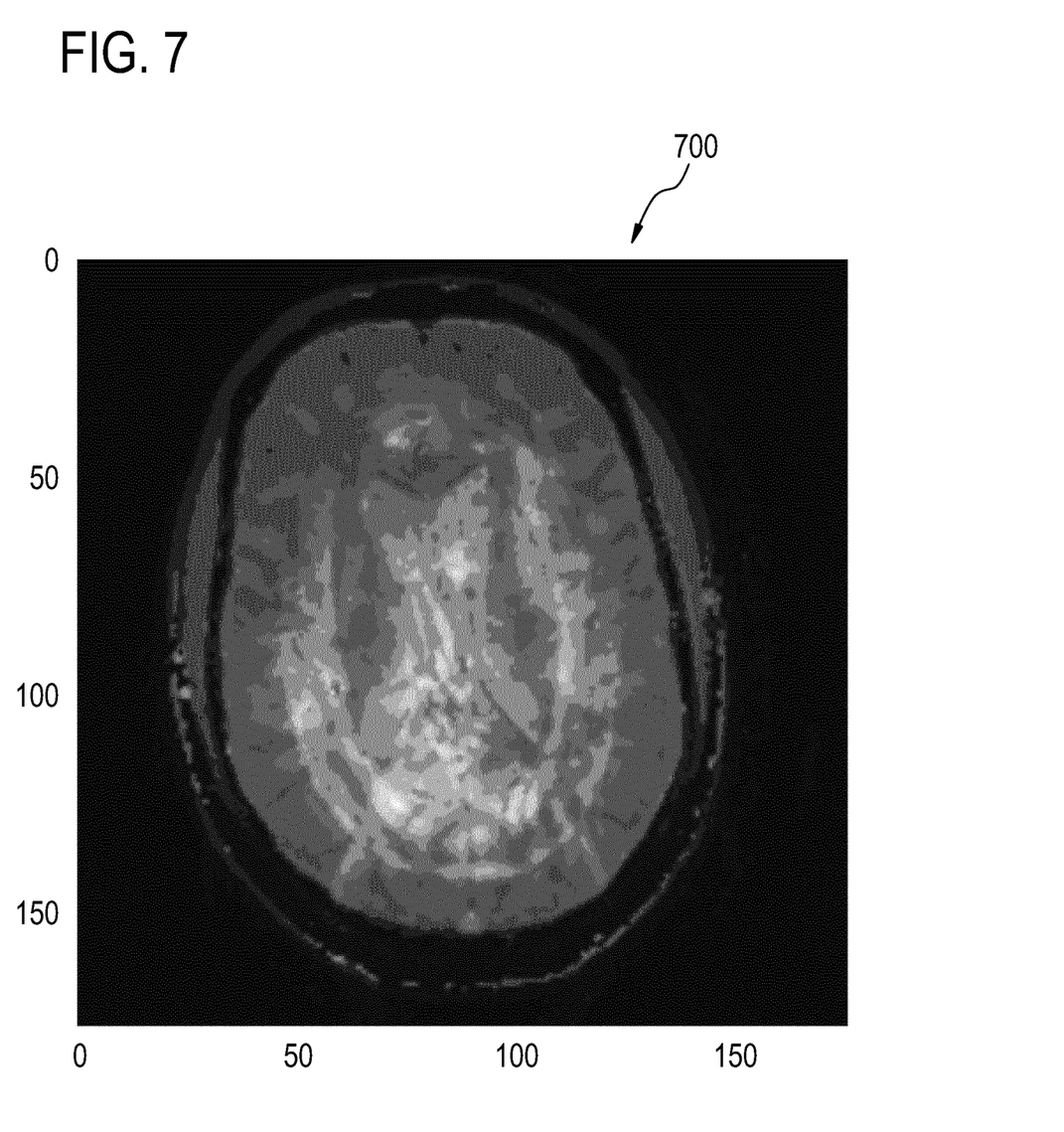
FIG. 7 shows a proton density map made using an MRF protocol.

FIG. 7 shows a proton density map 700 resulting from a spiral MRF acquisition and using a complex matching analysis. Artifacts due to high undersampling factor are translated into the proton density map 700.

Figure 8:
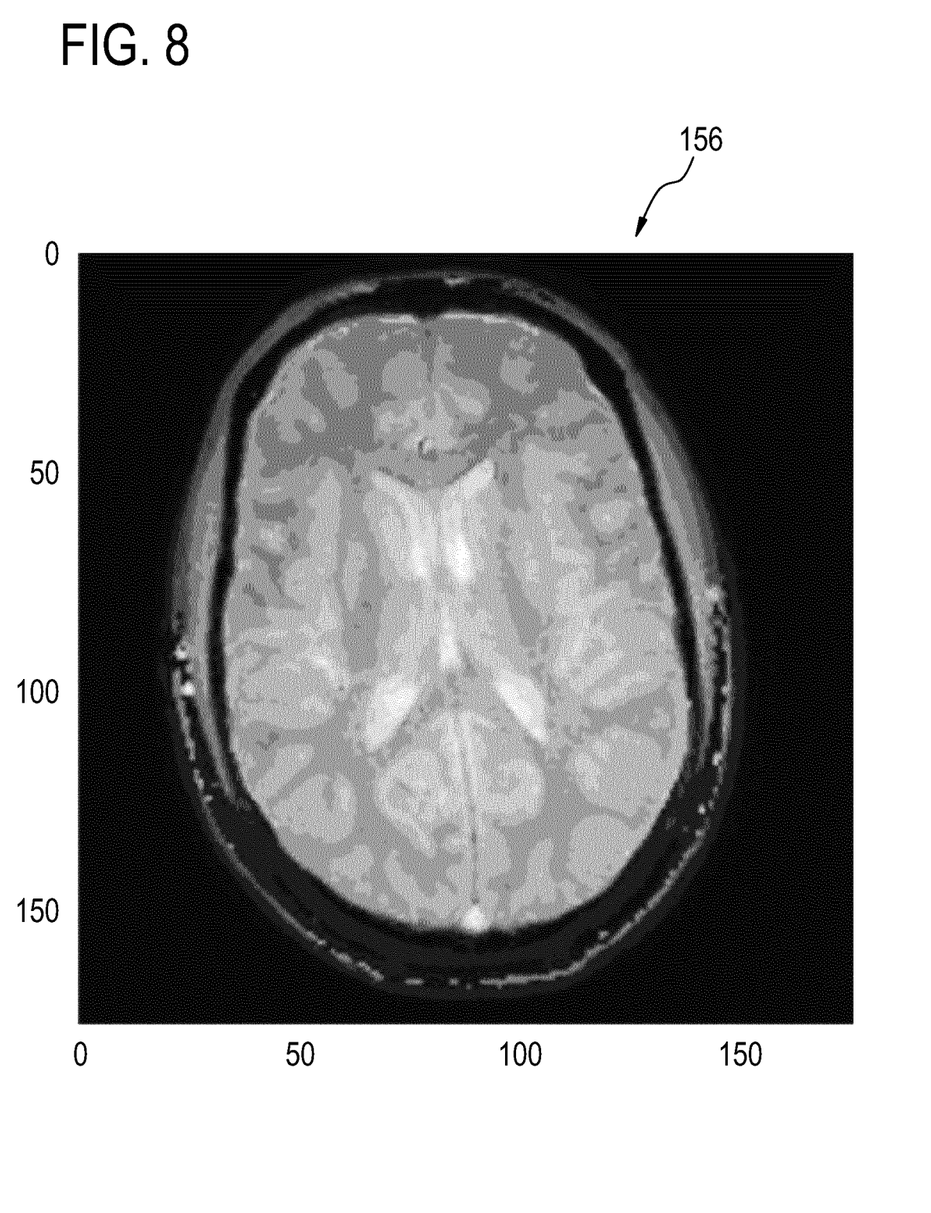
FIG. 8 shows a proton density map made according to an example herein using the same data as was used to construct the proton density map of FIG. 7.

FIG. 8 shows a proton density map 156 with reduced artifacts that was obtained from the same magnetic resonance fingerprinting dataset using a method where the MRF signal and the MRF fingerprinting dictionary were both transformed into Fourier space before matching. In FIG. 8 the intrinsic property that was mapped was the combined T1 and T2 values. The proton density map was calculated by calculating a scaling factor for each voxel between the model Fourier transformed MRF signal of the magnetic resonance fingerprinting dictionary and the Fourier transformed MRF signal. It can be seen that the proton density map 156 of FIG. 8 is far superior to the proton density map 700 of FIG. 7. The proton density map 156 of FIG. 8 clearly shows the anatomy of the subject's brain, whereas the proton density map 700 in FIG. 7 is highly distorted and is not useful clinically.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
132 user interface
134 computer memory
140 machine executable instructions
142 MRF pulse sequence commands
144 MRF magnetic resonance data
146 MRF signal
148 Fourier transformed MRF signal
150 Fourier transformed magnetic resonance fingerprinting dictionary
152 intrinsic property mapping
154 T1 and T2 mapping
156 proton density map
158 total water content map
160 intra-voxel content mapping
200 acquire MRF magnetic resonance data descriptive of a region of interest by controlling the magnetic resonance imaging system with the MRF pulse sequence commands, wherein the region of interest is divided into voxels
202 construct an MRF signal for each of the voxels using the MRF magnetic resonance data
204 construct a Fourier transformed MRF signal by Fourier transforming the MRF signal for each of the voxels
206 determine the least one intrinsic property for each of the voxels using the Fourier transformed MRF signal and the Fourier transformed magnetic resonance finger printing dictionary
300 construct a proton density map by calculating a scaling factor for each voxel between the modeled Fourier transformed MRF signal of the combined T1 and T2 value and the Fourier transformed MRF signal
302 calculate an intra-voxel component mapping for each of the voxels using the entries for the set of predetermined substances and the Fourier transformed MRF signal
304 calculate a Total Water Content map by scaling the proton density map using the intra-voxel component mapping
400 magnetic resonance imaging system
402 sample with known water content
404 water content scaling factor
500 MRF dictionary entry
600 aliasing artifacts
602 cutoff for fourier terms
604 fourier terms excluded
700 proton density map

The invention claimed is:

1. A magnetic resonance imaging system comprising:
a memory for storing machine executable instructions and MRF pulse sequence commands, wherein the MRF pulse sequence commands are configured for controlling the magnetic resonance imaging system to acquire MRF magnetic resonance data according to a magnetic resonance fingerprinting protocol, wherein the memory further contains a Fourier transformed magnetic resonance finger printing dictionary, wherein the Fourier transformed magnetic resonance finger printing dictionary comprises entries for at least one intrinsic property;
a processor for controlling the magnetic resonance imaging system;
wherein execution of the machine executable instructions causes the processor to:

acquire MRF magnetic resonance data descriptive of a region of interest by controlling the magnetic resonance imaging system with the MRF pulse sequence commands, wherein the region of interest is divided into voxels;

construct an MRF signal for each of the voxels using the MRF magnetic resonance data;

construct a Fourier transformed MRF signal by temporal Fourier transforming the MRF signal into its temporal frequency spectral distribution for each of the voxels; and determine the least one intrinsic property for each of the voxels using the Fourier transformed MRF signal and the Fourier transformed magnetic resonance finger printing dictionary, wherein the Fourier transformed MRF signal is truncated in the temporal frequency domainto a predetermined number of terms before determining the at least one intrinsic property.

2. The magnetic resonance imaging system of claim 1, wherein the at least one intrinsic property comprises combined T1 and T2 values, wherein determining the least one intrinsic property comprises determining a combined T1 and T2 value for each of the voxels using the Fourier transformed MRF signal and the matrix of combined T1 and T2 values in the Fourier transformed magnetic resonance finger printing dictionary.

3. The magnetic resonance imaging system of claim 2, wherein the Fourier transformed magnetic resonance finger printing dictionary comprises a modeled Fourier transformed MRF signal for each of the matrix of T1 and T2 values, wherein the method further comprises constructing a proton density map by calculating a scaling factor for each voxel between the modeled Fourier transformed MRF signal of the combined T1 and T2 value and the Fourier transformed MRF signal.

4. The magnetic resonance imaging system of claim 3, wherein the Fourier transformed magnetic resonance finger printing dictionary further comprises entries for a set of predetermined substances, wherein execution of the machine executable instructions causes the processor to calculate an intra-voxel component mapping for each of the voxels using the entries for the set of predetermined substances and the Fourier transformed MRF signal, wherein execution of the machine executable instructions further causes the processor to calculate a Total Water Content map by scaling the proton density map using the intra-voxel component mapping.

5. The magnetic resonance imaging system of claim 4, wherein the predetermined substances comprises fat, wherein calculating the intra-voxel component mapping comprises determining a fat map mapping, wherein execution of the machine executable instructions further cause the processor to correct the Total Water Content map using the fat mapping.

6. The magnetic resonance imaging system of claim 4, wherein the predetermined substances comprises cerebrospinal fluid, wherein execution of the machine executable instructions further causes the processor to identify CSF voxels at least partially by identifying voxels with a fraction of the cerebrospinal fluid in the intra-voxel component mapping above a predetermined threshold, wherein the scaling of the proton density map into the Total Water Content map is performed using a scaling factor determined using the CSF voxels.

7. The magnetic resonance imaging system of claim 4, wherein the predetermined substances comprises cerebrospinal fluid, wherein the intra-voxel component mapping for each of the voxels is calculated by maximizing an inner product of the Fourier transformed MRF signal with entries for the set of predetermined substances, wherein execution of the machine executable instructions further causes the processor to identify CSF voxels at least partially by indentifying voxels where the inner product between the Fourier transformed MRF signal and the entry for the cerebrospinal fluid in the Fourier transformed magnetic resonance finger printing dictionary is above a predetermined threshold, wherein the scaling of the proton density map into the Total Water Content map is performed using a scaling factor determined using the CSF voxels.

8. The magnetic resonance imaging system of claim 4, wherein the magnetic resonance imaging system comprises a sample with a predetermined water concentration, wherein execution of the machine executable instructions further causes the processor to identify voxels containing the sample in the intra-voxel component mapping, wherein the scaling of the proton density map into the Total Water Content map is performed using a scaling factor determined using voxels containing the sample.

9. The magnetic resonance imaging system of claim 4, wherein the predetermined substances comprises Grey Matter, wherein the predetermined substances comprises White Matter, wherein execution of the machine executable instructions causes the processor to:

calculate a GM mask by identifying voxels above a predetermined Grey Matter concentration in the composition mapping;

calculate a WM mask by identifying voxels above a predetermined White Matter concentration in the intra-voxel component mapping; and Correcting the proton density map with a bias field by fitting a function to the proton density map that reduces signal variation in voxels identified by the GM mask and the WM mask.

10. The magnetic resonance imaging system of claim 4, wherein the predetermined substances comprises cerebrospinal fluid, wherein the predetermined substances comprises Grey Matter, wherein the predetermined substances comprises White Matter, wherein execution of the machine executable instructions causes the processor to:

calculate a GM mask by identifying voxels above a predetermined Grey Matter concentration in the composition mapping;

calculate a WM mask by identifying voxels above a predetermined White Matter concentration in the intra-voxel component mapping;

calculate a pseudo proton density map using the concentration mapping; and

Correcting the proton density map with a bias field by fitting a function to the pseudo proton density map that reduces signal variation in voxels identified by the GM mask and the WM mask.

11. The medical imaging system of claim 2, wherein the memory further contains B1+ mapping pulse sequence commands for acquiring B1+ mapping magnetic resonance data according to a B1+ mapping magnetic resonance imaging protocol, wherein execution of the machine executable instructions further cause the processor to:

acquiring the B1+ mapping magnetic resonance data by controlling the magnetic resonance imaging system with the B1+ mapping pulse sequence commands;

construct a B1+ mapping using the B1+ mapping magnetic resonance data according to a B1+ mapping magnetic resonance imaging protocol; and correct the proton density map using the B1+ mapping.

12. The medical imaging system of claim 2, wherein the at least one intrinsic property comprises B1+ values, wherein the execution of the machine executable instructions cause the processor to:
reconstruct a B1+ map using the MRF magnetic resonance data and the Fourier transformed Magnetic Resonance Finger Printing Dictionary; and
correct the proton density map using the B1+ mapping.

13. The magnetic resonance imaging system of claim 1, wherein the Fourier transformed magnetic resonance finger printing dictionary further comprises entries for a set of predetermined substances, wherein determining the least one intrinsic property comprises calculating an intra-voxel component mapping for each of the voxels using the entries for the set of predetermined substances and the Fourier transformed MRF signal.

14. A method of operating a magnetic resonance imaging system, wherein the method comprises:
acquiring MRF magnetic resonance data descriptive of a region of interest by controlling the magnetic resonance imaging system with MRF pulse sequence commands, wherein the MRF pulse sequence commands are configured for controlling the magnetic resonance imaging system to acquire MRF magnetic resonance data according to a magnetic resonance fingerprinting protocol, wherein the region of interest is divided into voxels;
constructing an MRF signal for each of the voxels using the MRF magnetic resonance data;
constructing a Fourier transformed MRF signal by temporally Fourier transforming the MRF signal into its temporal frequency spectral distribution for each of the voxels; and
determine at least one intrinsic property for each of the voxels using the Fourier transformed MRF signal and a Fourier transformed magnetic resonance finger printing dictionary, wherein the Fourier transformed magnetic resonance finger printing dictionary comprises entries for the at least one intrinsic property, wherein the Fourier transformed MRF signal is truncated in the temporal frequency domain to a predetermined number of terms before determining the at least one intrinsic property.

15. A computer program product comprising machine executable instructions stored on a non-transitory computer readable medium for execution by a processor controlling a magnetic resonance imaging system, wherein execution of the instructions cause the processor to:
acquire MRF magnetic resonance data descriptive of a region of interest by controlling the magnetic resonance imaging system with the MRF pulse sequence commands, wherein the MRF pulse sequence commands are configured for controlling the magnetic resonance imaging system to acquire MRF magnetic resonance data according to a magnetic resonance fingerprinting protocol, wherein the region of interest is divided into voxels;
construct an MRF signal for each of the voxels using the MRF magnetic resonance data;
construct a Fourier transformed MRF signal by temporal Fourier transforming the MRF signal into its spectral temporal frequency distribution for each of the voxels; and
determine at least one intrinsic property for each of the voxels using the Fourier transformed MRF signal and a Fourier transformed magnetic resonance finger printing dictionary, wherein the Fourier transformed magnetic resonance finger printing dictionary comprises entries for the at least one intrinsic property, wherein the Fourier transformed MRF signal is truncated in the temporal frequency domain to a predetermined number of terms before determining the at least one intrinsic property.

* * * * *